United States Patent [19]

Abrams et al.

[11] Patent Number: 5,556,849

[45] Date of Patent: Sep. 17, 1996

[54] RUTHENIUM CONTAINING PHTHALOCYANIN PHOTOSENSITIZERS

[75] Inventors: Michael J. Abrams, Glenmore; Robert C. Brooks, Pottstown; Gerald E. Bossard, King of Prussia; Jean F. Vollano, Exton, all of Pa.

[73] Assignee: Johnson Matthey Public Limited Company, London, England

[21] Appl. No.: 232,146

[22] PCT Filed: Nov. 9, 1992

[86] PCT No.: PCT/GB92/02061

§ 371 Date: Sep. 12, 1994

§ 102(e) Date: Sep. 12, 1994

[87] PCT Pub. No.: WO93/09124

PCT Pub. Date: May 13, 1993

[30] Foreign Application Priority Data

Nov. 8, 1991 [GB] United Kingdom ............. 9123814

[51] Int. Cl.$^6$ ............. A61K 31/40; C07D 487/22
[52] U.S. Cl. ............. 514/185; 540/140; 514/410
[58] Field of Search ............. 540/125, 128, 540/136, 139, 140; 514/185

[56] References Cited

PUBLICATIONS

Hedtmann–Rein et al., Inorg. Chem., 26, 2647–51, 1987.
Martinsen et al., Inorg. Chem. 19, 2162–65 1980.

Primary Examiner—Mukund J. Shah
Assistant Examiner—Pavanaram K. Sripada
Attorney, Agent, or Firm—Cushman Darby & Cushman, LLP

[57] ABSTRACT

Water soluble salt or acid forms of a transition metal phthalocyanine of formula

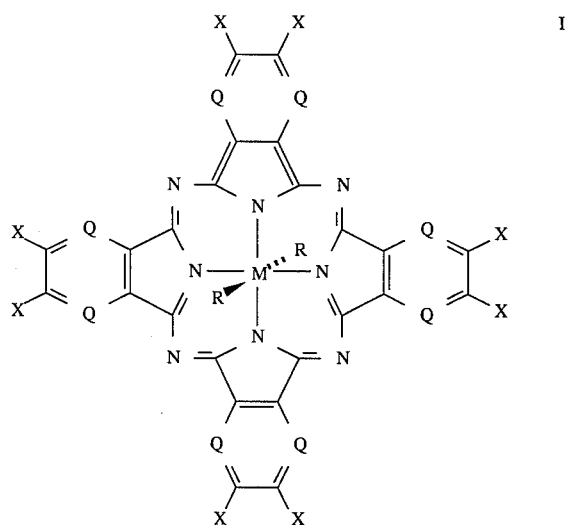

where M is a transition metal, X is H, alkyl, alkoxy, halide or X's together form —$C_4H_4$—, each R is a ligand with a solubilizing group, and Q is N or —CY— where Y is H, alkyl, alkoxy or halide, are surprisingly active in tests indicating photodynamic properties. Novel compounds, preparative methods and pharmaceutical compositions are included.

7 Claims, 3 Drawing Sheets

RUTHENIUM CONTAINING PHTHALOCYANIN PHOTOSENSITIZERS

This invention concerns photosensitizers, more particularly it concerns novel transition metal photosensitizers.

BACKGROUND

In the photodynamic therapy of cancer, certain dye compounds (eg, hematoporphyrin derivative, chloroaluminum phthalocyanine sulfonate) are administered to a tumor-bearing subject. To some extent these dye compounds are taken up by the tumor tissue and upon selective irradiation with the appropriate light source the tumor tissue is destroyed via the dye mediated photo-generation of toxic species such as single; oxygen, A large number of phthalocyanine (Pc) derivatives have been proposed as potential photodynamic therapeutic (PDT) agents. Most biological studies on Pc compounds related to PDT have been conducted with water soluble sulfonated metallo-phthalocyanines (as reported by Rosenthal. I. Photochem Photobiol 53(6). 859–870. (1991). These compounds are generally obtained by sulfonation of the appropriate metallo-phthalocyanine or by template synthesis using the appropriate sulfonated precursors and a metal salt. Both template synthesis and direct sulfonation results in mixtures of Pc's containing a variety of isomers and/or different degrees of sulfonation. This is a particular disadvantage with respect to pharmaceutical applications in that drug regulatory agencies are increasingly stringent in their requirements for substantially pure compounds.

Metallated Pc's have been found to have superior photosensitizing activity compared to metal-free Pc's when the metal is a main group element having a filled d shell (eg. Al. Zn, Sn. In). It has been reported by Chan, W S. et al. Photothem Photobiol. 45, 757–761 (1987), that transition metal complexes of Pc's have been found to be inactive (eg. Cu, Co, Ni. VO, Pal).

There remains a need for novel photosensitizers which can be prepared in isomerically pure form and which show a good level of activity.

The present invention provides novel transition metal phthalocyanine-type derivatives of formula I.

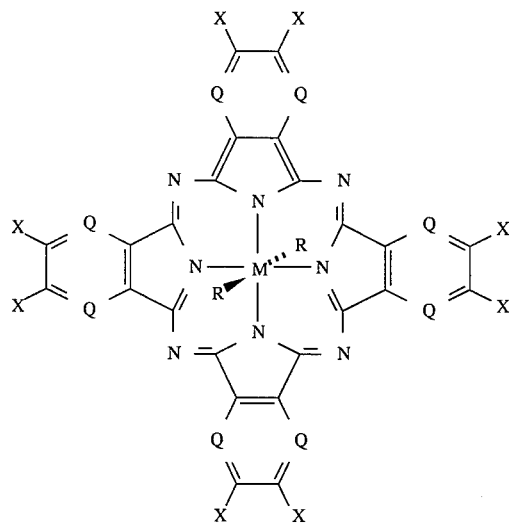

wherein M is a second or third row transition metal with a $d^6$ low-spin electronic configuration, X is hydrogen, alkyl, alkoxy, halide or adjacent X's may together form —$C_4H_4$—, each R is a ligand selected from phosphine, mine, amine, isocyanide, nitrile, thiolate, hydrazine, cyanide, thiocyanate, phenolate, sulphide and analine groups having a water-solubilizing moiety, and Q is nitrogen or —CY—, where Y is hydrogen, alkyl, alkoxy or halide, in water-soluble salt or acid form.

Preferably. M is selected from Ru, Rh, Os or Ir. Suitable ligands R incorporate triphenylphosphine or triethylphosphine, and solubilizing groups are suitably sulfonate or carboxylate groups. When R incorporates an amine, it may be a straight or branched chain amine, or an aromatic amine such as pyridine. Preferred R ligands are triphenyl-phosphine mono-, di- or tri-sulfonate, 4-pyridine ethanesulfonate, 3-pyridine sulfonate, triphenylphosphine monocarboxylate, 4-isocyanobenzoate, nicotinic acid, taurine or amino acids.

Preferably, the compound is in salt form, with counterions which are desirably $K^+$, $Na^+$ or quaternary ammonium.

The compounds of formula I are novel, and may be prepared by a process comprising reacting a metal phthalocyanine compound of formula II,

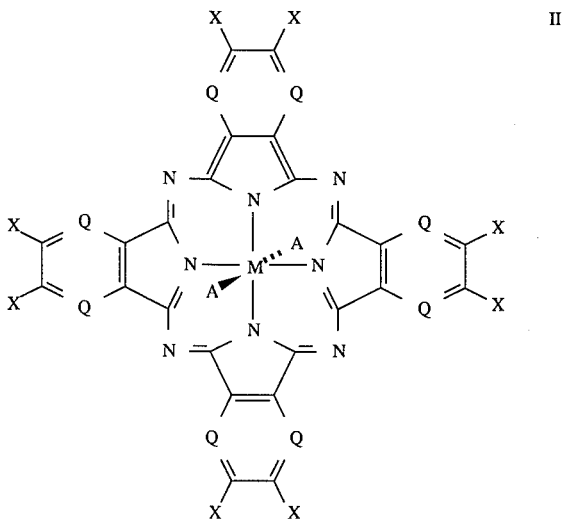

wherein M, Q and X are as define above, and A is an amine, preferably a pyridine group, CO (carbon monoxide) or a co-ordinating solvent, for example benzonitrile, with a salt of the ligand R, and isolating the product compound of formula I.

Many of the reactants of formula II, and the salts of ligand R, are known from the literature. However, compounds of formula II in which A is ammine, benzonitrile, methylcyanide or another co-ordinating solvent, are believed to be novel and form part of the present invention. Although such compounds may be prepared by methods analogous to those in the art, the invention further provides a method of producing said novel compounds of formula II in which A is benzonitrile by reacting M phthalocyanine bis(ammine) with benzonitrile. The ammine complex may be prepared by reacting $MCl_3$. $xH_2O$, where x is 2 or 3, with phthalonitrile, and then with ammonia.

Suitably, the starting metal phthalocyanine or naphthalocyanine is mixed in an organic solvent, such as mixed xylenes, with an excess, for example 2–10 fold stoichiometric, of an organic-soluble form of the water solubilizing ligand, under an inert atmosphere, such as argon. The reaction is carried out desirably by heating, for example at reflux for about two days. The product may be isolated by the addition of a co-solvent to the reaction mixture. If required, the solubility of the product may be enhanced by exchanging the counterions, in generally known It is believed that the present invention, by incorporating a water solubilizing axial ligand, instead of the conventional substitution at the periphery of the Pc to obtain water solubility, permits the synthesis of isomerically pure compounds. The novel compounds have been found to be active in in vitro and in vivo tests for photosensitizing activity described hereafter.

The present invention also provides a pharmaceutical composition comprising a compound of formula I in admixture or association with a pharmaceutically acceptable carrier or diluent. The invention is also considered to include a method of treatment of a mammal having a tumor susceptible to photodynamic treatment, wherein the mammal is administered an effective dose of a compound of formula I or a pharmaceutically acceptable salt form thereof, and the tumor is subjected to light radiation.

The pharmaceutical compositions may be formulated according to well-known principles, and may desirably be in the form of unit dosages determined in accordance with conventional pharmacological methods. The unit dosage forms may provide a daily dosage of active compound in a single dose or in a number of smaller doses- Dosage ranges may be established using conventional pharmacological methods and are expected to lie in the range 1 to 50 mg/kg of body weight. Other active compounds may be used in the compositions or administered separately or supplemental therapy may be included in a course of treatment for a patient. The pharmaceutical compositions may desirably be in the form of solutions or suspensions for injection, or in forms for topical application, including application in the oral cavity. Suitable carriers and diluents are well known in the art, and the compositions may include excipients and other components to provide easier or more effective administration.

Following administration to the patient, photodynamic therapy may be carried out in conventional manner, using light sources and delivery systems that are known in the art. See, for example, Phys Med Biol. (1986). 31. 4. 327–360.

Figure 1:
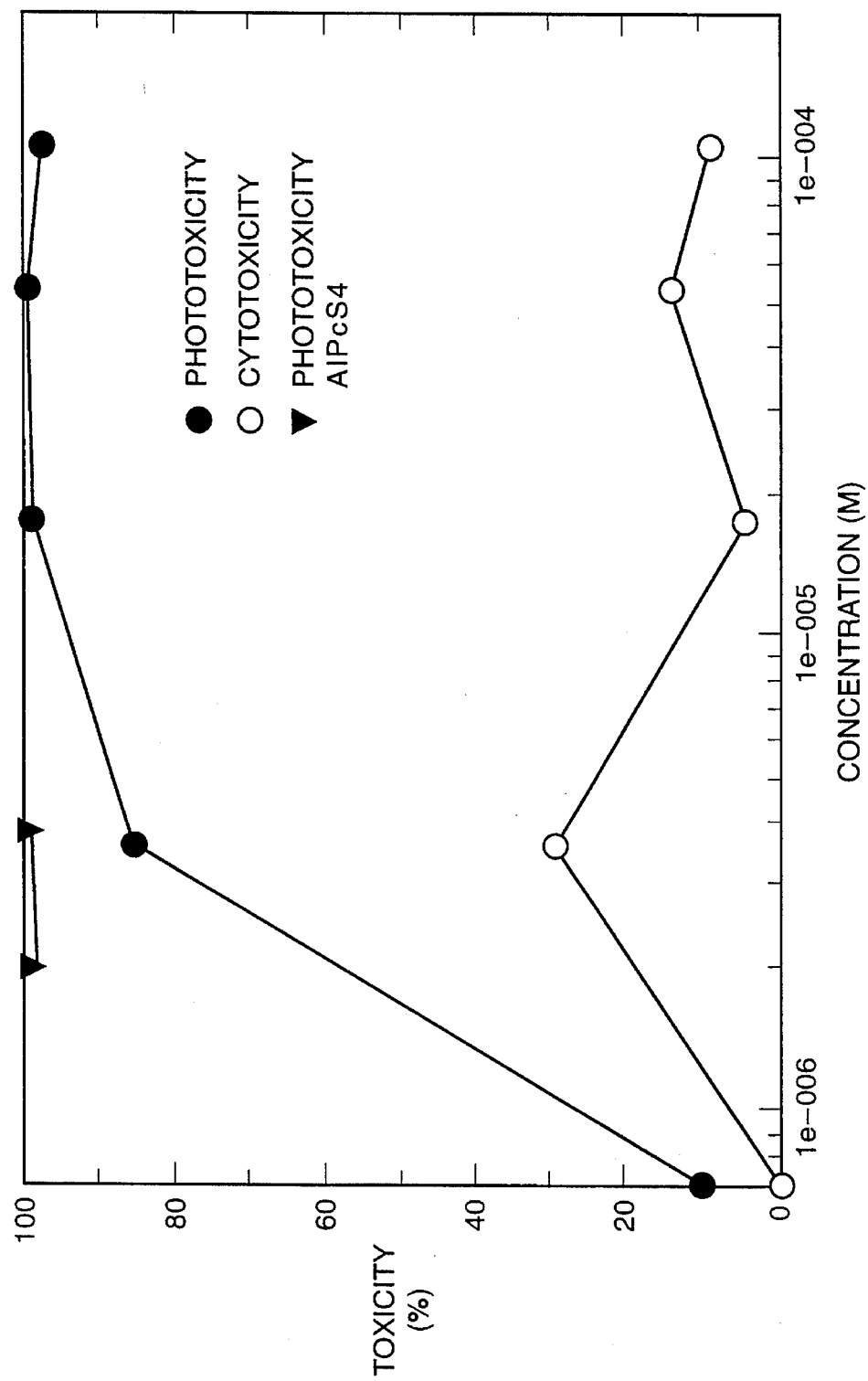
FIG. 1 illustrates in vitro results obtained with a compound of the invention in comparison to a prior art compound.

The invention will now be illustrated by the following Examples, which particularly describe aspects of the invention but in no way limit its scope.

The sodium salt of triphenylphosphine monosulfonate [Na(I)] and 4-pyridine ethanesulfonic acid were obtained commercially, and Ru(Pc)(pyridine)$_2$ was prepared by a literature method, (N P Farrell, et al. Inorg Chim Acta, 28, L144–L146. 1978).

EXAMPLE 1

K$_2$[Ru(Pc)bis(triphenvlphosphine monosulfonate)]trihydrate (Compound A)

The tetrabutylammonium salt of triphenylphosphine monosulfonate [TBA(I)] was prepared by mixing 0.2 g of Na(I) and 0.23 g of tetrabutyl-ammonium bisulfate [TBA(HSO$_4$)]in basic aqueous solution and extracting TBA(I) into methylene chloride. After washing the organic phase with water, solvent was removed to yield 0.34 g of TBA(I) as a yellow oil.

TBA(I) (0.34 g, 0.58 mmol) and Ru(Pc)(Py)$_2$ (0.15 g. 0.20 mmol) were admixed in a mixed xylene solvent (10 ml) and the mixture heated to reflux for two days. At several times during the reaction period a portion of solvent was allowed to evaporate to remove pyridine and sufficient xylenes added to maintain the reaction volume at 10 ml. Upon cooling to room temperature, diethyl ether was added to precipitate a blue solid. This material was dissolved in a minimum volume of ethanol and filtered. To this solution was added potassium acetate (0.5 g) in 5 ml of ethanol. The resulting crystalline blue solid was collected, washed with ethanol and diethyl ether and air dried. Yield =0.22 g. 78% based on Ru.

Analysis for $C_{68}H_{50}K_2N_8P_2O_9RuS_2$ Calc: C, 57.13; H. 3.53; N, 7.84 Found: C, 57.13; H. 3.63; N, 8.05

EXAMPLE 2

K$_2$[Ru(Pc)bis(4-pyridineethanesulfonate)]tetrahydrate

The tetrabutylammonium salt of 4-pyridine ethanesulfonate [TBA(II)]was prepared by mixing TBA[HSO$_4$](6 g) and 3 g of the pyridine in water and adding 30% NaOH solution until the pH was greater than 11. This gave an oil which was subjected to rotary evaporation with a mixed xylene solvent. The residue was dissolved in methylene chloride, filtered and extracted three times with water. Removal of solvent yielded a pale green oil.

TBA(II) (0.72 g, 1.68 mmol) and Ru(Pc)(Py)$_2$ (0.14 g, 0.18 mmol) were dissolved in 25 ml of a mixed xylene solvent and the mixture heated to reflux under N$_2$ for two days, giving a near lorless solution. The reaction was cooled to room temperature and the resulting blue solid collected. Yield of [TBA]$_2$[Ru(Pc) (4-pyridine ethanesulfonate)$_2$]=0, 23 g. This material was dissolved in ethanol (12 ml) and filtered. Addition of potassium acetate (0.35 g) in ethanol (3.5 ml) resulted in the precipitation of a blue solid that was collected, washed with ethanol and diethyl ether and air dried. Yield =0.174 g, 87% based on Ru.

Analysis for $C_{46}H_{40}K_2N_{10}O_{10}RuS_2$ Calc: C, 48.62; H. 3.55; N, 12.33 Found: C, 48.46; H. 3.64: N. 12.06

EXAMPLE 3

Na$_2$[Ru(Pc)bis(taurine)]hexahydrate

Taurine (0.28 g) and 0.20 ml of 10N NaOH in water were stirred in 10 ml of ethanol for 2 hours. RuPc(Benzonitrile)$_2$ (0.30 g) and 10 ml of toluene were added and the resulting mixture was refluxed under nitrogen overnight. The solvents were removed and the residue washed with toluene and methylene chloride. The remaining solid was dissolved in methanol and the solution filtered. The addition of toluene caused the product to precipitate. The blue solid was collected, washed with methylene chloride and air dried. Yield =0.25 g (70%).

Analysis for $C_{36}H_{40}N_{10}Na_2O_{12}RuS_2$ Calc: C, 42.56; H. 3.97; N, 13.79 Found: C, 42.55; H. 3.85: N, 13.59

Many other compounds within the scope of the invention were prepared using analogous methods to those of the above samples. The structures are given in abbreviated form in the Table that follows the in vitro testing section hereinafter. Most of the compounds are characterised by their light absorption maxime ($\lambda_{max}Q$) and molar extinction coefficients ($\epsilon M^{-1}cm^{-1}$).

Starting Materials
Ruthenium phthalocyanine bis(ammine)
Ruthenium trichloride hydrate [$RuCl_3 \cdot xH_2O$](2.32 g) was heated in 25 ml of pentanol until the solution had turned completely blue and all the water had been distilled out. This solution was added over 3 minutes to 6.5 g of phthalonitrile and 0.54 g of hydroquinone dissolved into 20 ml of boiling pentanol. The resulting orange suspension was refluxed for 3 days under a slow purge of ammonia gas. The reaction was cooled to room temperature and the purple solid filtered off. The solid was washed with methanol and methylene chloride, repeatedly, until the washings were nearly colourless. The solid was air dried. The yield of 6.58 g of $RuPc(NH_3)_2$ was used without further purification.

Ruthenium phthalocyanine bis(benzonitrile)monohydrate

The $RuPc(NH_3)_2$ was refluxed in 75 ml of PhCN for one day under nitrogen. The mixture was diluted to 1 litre with hot chloroform and stirred at reflux for one hour. The solution was filtered hot and 3l of methanol was added to the filtrate. A first crop of product, 5.39 g filtered off after 16 hours. A second crop was isolated by reducing the filtrate to 2.5l by boiling. This gave an additional 1.48 g of product. The total yield was 6.87 g. 84%, of purple crystals.

Analysis for $C_{46}H_{28}N_{10}ORu$ Calc: C, 65.9; H. 3.37; N. 16.72 Found: C, 65.58; H. 3.33; N. 16.78

Photochemical and Biological Studies
Singlet Oxygen Generation

Singlet oxygen generation was determined by the photodegradation of nitrosoanaline dye following the method of Kraljic and Mohsni (*Photochem PhotoBiol*, 28. 577–581 (1978). A stock buffer of oxygen saturated 50 mM Na phosphate pH =7.5. 16 mM imidazole (recrystallized from benzene) was mixed 1:1 with the test compound in water and 2.5 µl/ml of N,N-dimethyl-p-nitrosoanaline was added in the dark.

100 µl of the test solution was plated out in triplicate on a Coming 96 well plate and exposed to light from a Kodak slide projector with an unfiltered 300W 82 U FHS incandescent lamp, producing black body radiation at 1700 K. at a distance of 35 cm from the plate, which is maintained at 4° C. in a cold box for 15 minutes of irradiation.

Decomposition of the nitroso dye is followed at 450 nm with a Dynatech MR600 microplate reader (test λ450 nm, ref λ540 nm).

Figure 3:
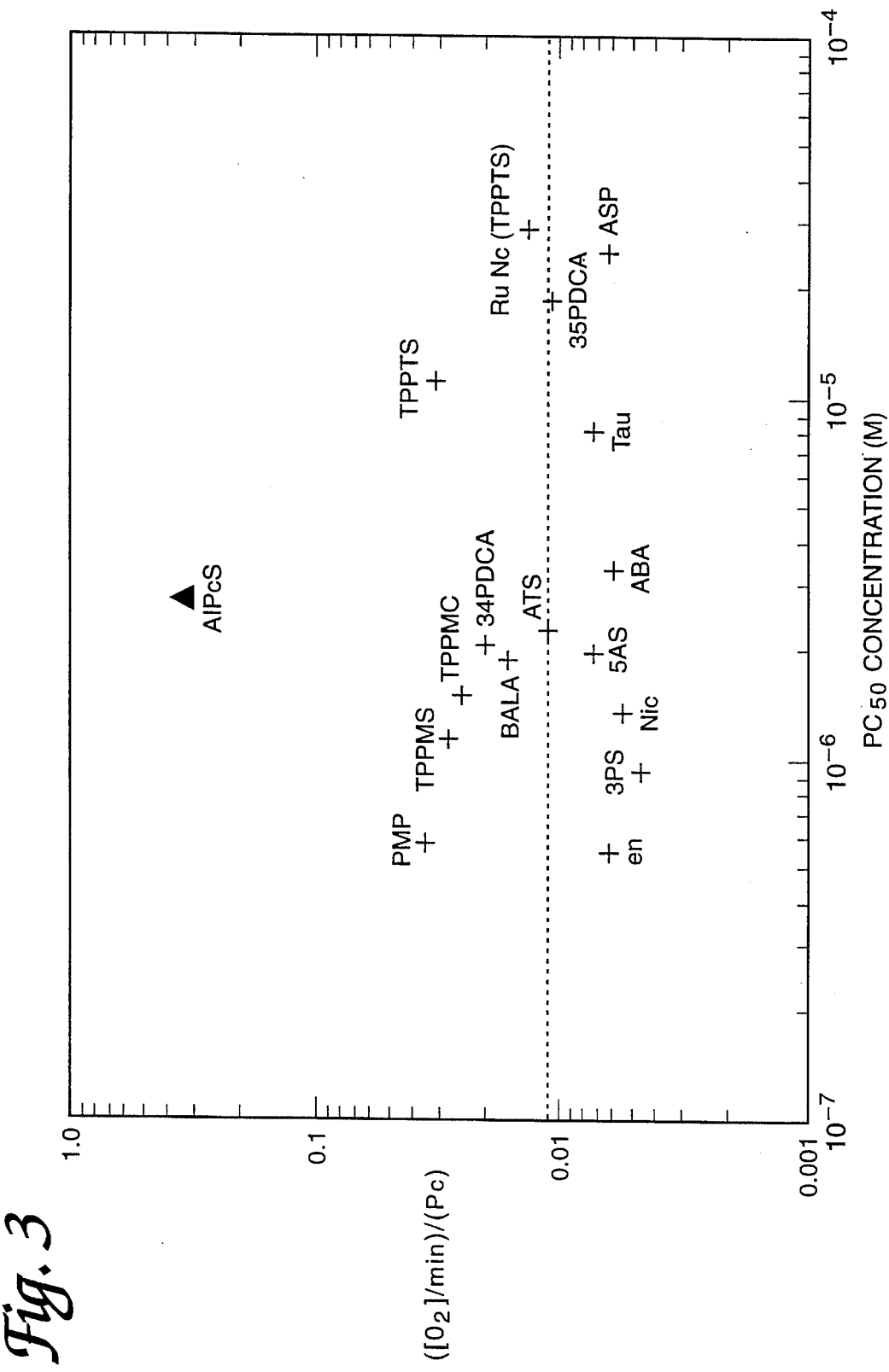
FIG. 3 illustrates the relationship of singlet oxygen production to the $PC_{50}$ of various compounds according to the invention in comparison with a prior compound."

FIG. 3 attached shows the relationship of singlet oxygen production to the $PC_{50}$ of various ruthenium phthalocyanine compounds according to the invention and aluminjure phthalocyanine sulphonate. In the Figure the abbreviations for the ligands are used to represent the entire molecule. eg $RuPc(TPPMS)_2$ =TPPMS. A full list of abbreviations is given below.

The compounds described produce singlet oxygen at a rate which varies ten-fold with respect to molar sensitizer concentration. However, there is no correlation of the rate of singlet oxygen production and the effectiveness of the compounds as measured by the $PC_{50}$ values for the compounds. The rate of singlet oxygen production of aluminium phthalocyanine sulphonate is on the order of one or two logs better than some of the sensitizers listed yet the effectiveness of many of these compounds described are higher than the aluminium compound. This suggests improved uptake of these compounds or a novel site of action within the cells.

Phototoxicity (Light)

Phototoxicity experiments follow the procedure used by Glassberg et al. (Glassberg. E. Lewandowski. L. Lask. G and Vitto.J, *J Invest Dermatol*. 94. 604–610 (1990). Adherent cells (HeLa RCA. SKOV OVCAR) are plated at 4×10$^4$ cells/well in a 94 well Coming microtiter plate in RPMI 1640 and FCS for four hours. The sensitizer is added in the same media at a set concenuation range in triplicate, and the cells are incubated for 24 hours at 37° C. with 5% $CO_2$.

The media is removed and the cells washed three times with D-PBS. and then covered with D-PBS (200 µl ) and exposed to light from the same source used in the singlet oxygen assay. Irradiation time can be varied between one and fifteen minutes, at which time the D-PBS is removed and fresh media RPMI-1640 +FCS is added and the cells incubated as before for sixteen hours.

$^3$H-thymidine (50 µl ) in RPMI-1640 +FCS is added and the cells are incubated for a further four hours, at which time they are harvested on glass filter mats and the incorporation of 3H-thymidine is determined relative to an untreated (no sensitizer added) control.

Cytotoxicity

This follows the procedure for phototoxicity except that the cells are never exposed to light. The assay is relative to a non-treated control.

Results

The in vitro results obtained with Compound A. $K_2[RuPc(TPPMS)_2]$, are shown in comparison to chloroaluminum phthalocyanine suffonate obtained from Porphyrin Products. Logan. Utah. in FIG. 1 of the attached drawings.

Compounds according to the invention were assessed and characterised by their light absorption maxima, and their molar extinction coefficients according to conventional test procedures. Most of the compound were tested for their biological activity according to conventional test procedures in the art. The $PC_{50}$ represents phototoxic concentration 50%. which is the concentration of compound when exposed to a light dose as described herein, causes a 50% reduction in cancer cell growth vs an untreated control population. The phototoxicity index. PI, is the ratio of the $PC_{50}$ to the cytotoxic concentration 50%. where the growth is reduced by 50% without a light dose being given.

The results are listed in the Table below: the abbreviations used to identify the compounds are given after the Table. $PC_{50}$ is determined by a relatively simple in vitro assay on a cellular level, which is generally indicative of photosensitizing activity. However, since some photosensitizers function on a tissue/organ level, inactivity in the $PC_{50}$ assay as shown by certain compounds below does not determine that the compounds are not active.

| Compound | $\lambda_{max}Q$ | $\epsilon$ M$^{-1}$cm$^{-1}$ | $PC_{50}$ | PI |
| --- | --- | --- | --- | --- |
| $RuPc(TPPTS)_2$ | 650 W | $8.74 \times 10^4$ | $1.13 \times 10^5$ | >15 |
| $RuPc(TPPMS)_2$ (Ex 1) | 650 W | $8.82 \times 10^4$ | $1.14 \times 10^{-6}$ | >100 |
| $RuPc(TPPMS)_2$ | 652 W | $9.03 \times 10^4$ | | |
| $RuPc(3PS)_2$ | 630 W | $7.36 \times 10^5$ | $9.29 \times 10^{-7}$ | >109 |
| $RuPc(Nic)_2$ | 630 W | $6.48 \times 10^5$ | $1.26 \times 10^{-6}$ | >79 |
| $RuPc(Tau)_2$ (Ex 3) | 623 M/634 W | $7.98 \times 10^4$ | $9 \times 10^{-6}$ | >1.1 |
| $RuPc(5AS)_2$ | 635 W | $6.65 \times 10^4$ | $2 \times 10^{-6}$ | >10 |

-continued

| Compound | $\lambda_{max}Q$ | $\epsilon\ M^{-1}cm^{-1}$ | $PC_{50}$ | PI |
|---|---|---|---|---|
| RuPc(TAC)$_2$ | 633 W | $3.11 \times 10^4$ | $8.6 \times 10^{-7}$ | 2.9 |
| RuPc(ABA)$_2$ | 638 W | $7.25 \times 10^4$ | $3.5 \times 10^{-6}$ | 8.8 |
| RuPc(ATS)$_2$ | 636 W | $7.48 \times 10^4$ | $2.27 \times 10^{-6}$ | >4.4 |
| RuPc(CBA)$_2$ | 650 W | $9.76 \times 10^4$ | $4.2 \times 10^{-7}$ | 10.2 |
| Ru(oMe)$_8$Pc(35PDCA$_2$) | 641 W | $6.33 \times 10^4$ | Inactive | 1 |
| RuPc(ASP)$_2$ | 635 W | $8.99 \times 10^4$ | $2.6 \times 10^{-5}$ | >3.8 |
| RuPc(ARG)$_2$ | 635 W | $1.03 \times 10^5$ | $1.8 \times 10^{-5}$ | 1.3 |
| RuF$_{16}$Pc(Nic)$_2$ | 635 W | $5.57 \times 10^4$ | Inactive | 1 |
| RuPc($\beta$-ALA)$_2$ | 635 W | $1.05 \times 10^5$ | $1.9 \times 10^{-6}$ | 26.3 |
| RuPc(34PDCA)$_2$ | 630 W | $5.88 \times 10^4$ | $2.1 \times 10^{-6}$ | 47.6 |
| RuPc(35PDCA)$_2$ | 632 W | $4.84 \times 10^4$ | $1.8 \times 10^{-5}$ | >5.6 |
| RuPc(PMP)$_2$ | na | na | $5.8 \times 10^{-7}$ | 25.8 |
| RuNc(TPPTS) | 650 W | na | $3 \times 10^{-5}$ | 3 |
| RuNc(TPPTS)$_2$ | 720 W | na | $>1 \times 10^{-4}$ | na |
| RuNc(TPPMS)$_2$ | 734 W | $5.4 \times 10^4$ | $2.7 \times 10^{-6}$ | 1.6 |
| RuNc(Nic)$_2$ | 762 W | $1.69 \times 10^5$ | $1.05 \times 10^{-7}$ | 22.2 |
| RupyrPc(Nic)$_2$ | 625 W | $4.51 \times 10^4$ | Inactive | 1 |
| RuPc(py)(TPPMC) | 644 W | $5.46 \times 10^4$ | na | na |
| Ru(TPPMC)$_2$ | na | na | $1.5 \times 10^{-6}$ | 20 |
| RuNc($\beta$-ALA)$_2$ | 730 W | $3.65 \times 10^4$ | $9.6 \times 10^{-7}$ | 1.51 |
| RuNc(3PS)$_2$ | 730 W | $8.3 \times 10^4$ | $4.6 \times 10^{-7}$ | 32.6 |
| RuPc(PES)$_2$ (Ex 2) | 632 W | $7.25 \times 10^4$ | Inactive | 1 |

| Abbreviations | |
|---|---|
| Core Structures | |
| RuPc | Ruthenium(II)phthalocyanine |
| Ru(oMe)$_8$Pc | Ruthenium(II)-2,3,9,10,16,17,23,24-octamethyl-phthalocyanine |
| RuNc | Ruthenium(II)naphthalocyanine |
| RuF$_{16}$Pc | Ruthenium(II)-1,2,3,4,8,9,10,11,15,16,17,18,22,23,-24,25-hexadeca-fluorophthalocyanine |
| RupyrPc | Ruthenium(II)-1,4,8,11,15,18,22,25-octaaza-phthalo-cyanine |
| Ru(pMeO)$_8$Pc | Ruthenium(II)-1,4,8,11,15,18,22,25-octamethoxy-phthalocyanine |
| Axial Ligands | |
| TPPTS | Sodium triphenylphosphine-m-trisulfonate |
| TPPMS | Potassium triphenylphosphine-m-sulfonate |
| TPPMC | Sodium triphenylphosphine-m-carboxylate |
| 3PS | Sodium 3-pyridinesulfonate |
| Nic | Nicotinic acid |
| PMP | Sodium 3-pyridinemethylphosphate |
| 34PDCA | 3,4-pyridinedicarboxylic acid |
| 35PDCA | 3,5-pyridinedicarboxylic acid |
| Tau | Sodium 2-aminoethanesulfonate (Taurine) |
| 5AS | 5-aminosalicylic acid |
| TAC | Potassium thio-acetate |
| ABA | 3-aminobenzoic acid |
| ATS | Potassium 4-amino-2-toluenesulfonate |
| CBA | 3-cyanobenzoic acid |
| ASP | Potassium aspartate |
| ARG | Arginine |
| $\beta$-ALA | $\beta$-Alanine, Potassium salt |
| PES | Potassium 4-pyridine ethanesulfonate |
| Miscellaneous | |
| W | Water |
| M | Methanol |
| i | Insoluble |
| DW | Decomposes in Water |
| na | not analyzed |

In Vivo Studies

The photodynamic threshold dose in normal rat liver was used as a model. This has been developed by Singh and Wilson at McMaster University and used to study both chloroaluminum phthalocyanine sulfonate (ASPc) and photofrin (Patterson, M S, et at, *Photochem Photobiol*, 51,343–349, 1990, and Farrell, T J, et at, *Proc SPIE* 1426, 146–155, 1991).

Procedure

1. Inject compound at 2.5 mg/ml into tail vein of adult Wistat rats at doses of 5, 10.20 mg/kg.

2. 24 hours later expose liver by laparotomy and irradiate surface at up to four locations with a 5 mm diameter lightbeam from an argon-dye laser operating at 650 nm: incident power =40 m Watt: incident fluence rate =200 mW cm$^{-2}$: treatment time =5 or 10 minutes (60. 120 Joules cm$^{-2}$).

3. 24 hours later inject Evans Blue iv, sacrifice at 15 minutes, section Liver through each radiation spot and measure depth of necrosis as indicated by dye exclusion.

Results

Figure 2:
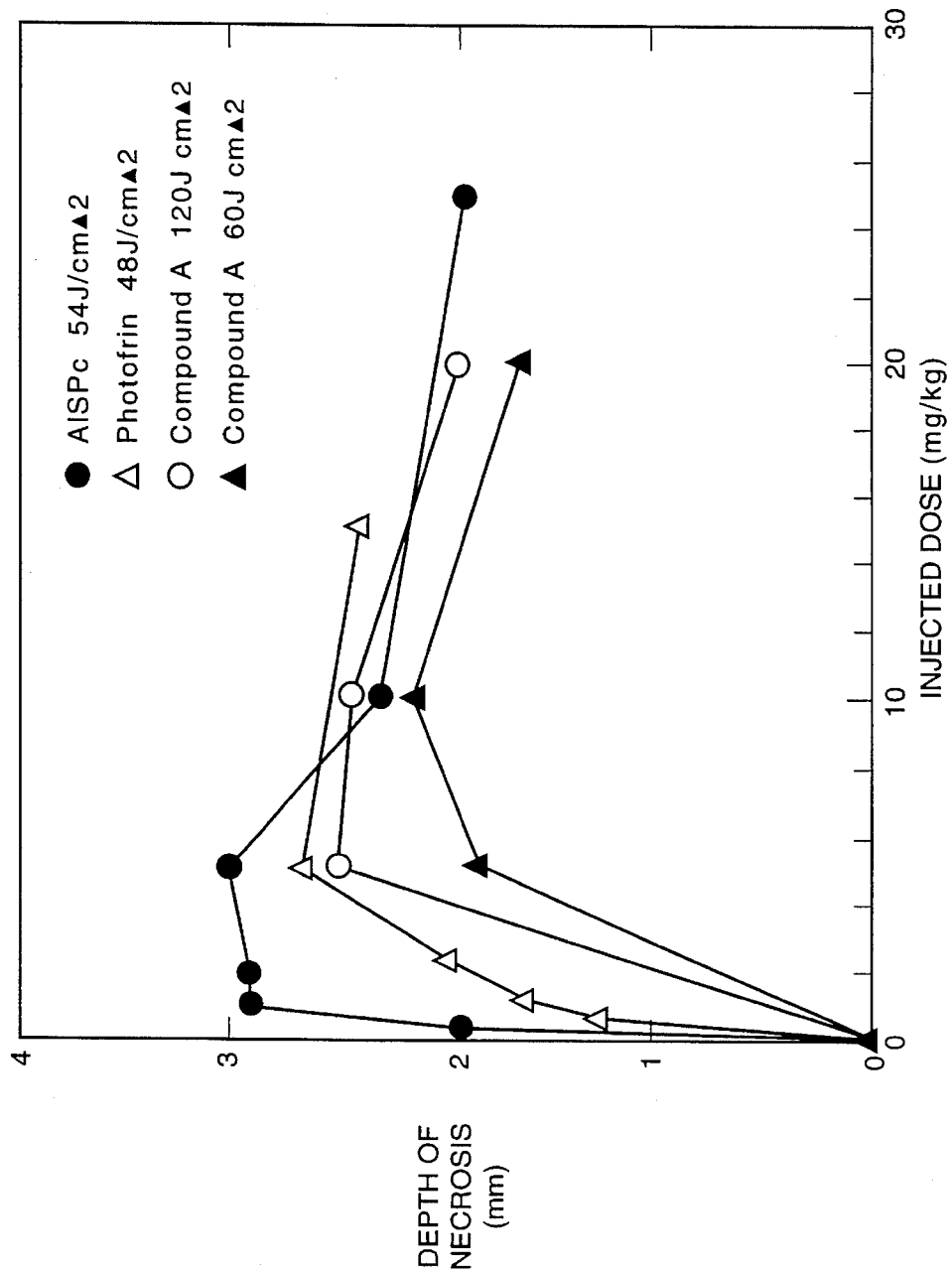
FIG. 2 graphically illustrates the depth of necrosis at varying dosage levels for various compounds including a compound according to the invention.

The measured depths of necrosis are given in Table 1 below and shown in FIG. 2 together with the most comparable data for AISPc and Photofrin (which were administered ip not iv). Compound A is clearly shown to be photodynamically active in vivo. The depths of necrosis at similar drug and light levels are comparable to those with previously studied agents, including the current clinical photosensitizer. Photofrin.

TABLE 1

| Injected Dose Compound A | Incident Fluence (J cm$^{-2}$) | Depth of Necrosis (mm) |
|---|---|---|
| 0 | 60, 120 | 0* |
| 5 | 60 | 1.86 ± 0.34 |
| 5 | 120 | 2.5 ± 0.0 |
| 10 | 60 | 2.16 ± 0.10 |
| 10 | 120 | 2.41 ± 0.16 |
| 20 | 60 | 1.66 ± 0.05 |
| 20 | 120 | 1.94 ± 0.04 |

*No-drug control is established in previous studies, and produced no measurable necrosis at these fluence rates and fluences.
± Standard Deviation based on two irradiation spots in each of two in each of two animals per data point.

We claim:

1. A compound which is a transition metal phthalocyanine or naphthalocyanine derivative of formula I

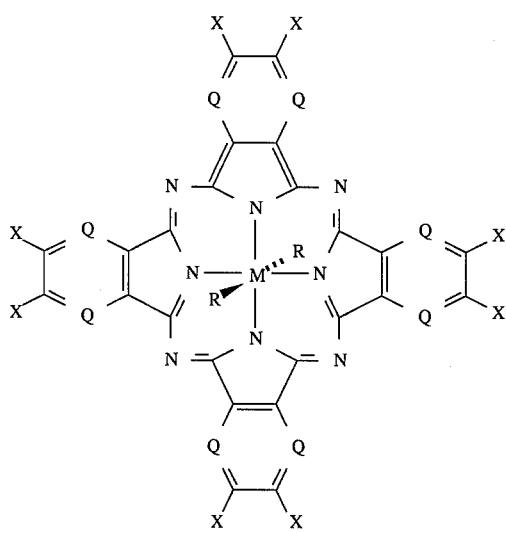

wherein M is Ru

X is hydrogen, alkyl, alkoxy, halide or adjacent X's may together form —$C_4H$—$_4$, each R is a ligand selected from phosphine, arsine, amine, isocyanide, nitrile, thiolate, hydrazine, cyanide, thiocyanate, phenolate, sulphide and aniline groups having a water-solubilizing moiety, and Q is nitrogen or —CY—, where Y is hydrogen, alkyl, alkoxy or halide, in water-soluble salt or acid form.

2. A compound according to claim 1, wherein R is selected from the group consisting of triphenylphosphine, triethylphosphine and amine having one or more sulfonate or carboxylate groups.

3. A compound according to claim 2, wherein R is selected from the group consisting of triphenylphosphine and pyridine having one or more sulfonate or carboxylate groups.

4. A compound according to any one of the preceding claims, wherein the phthalocyanine structure is substituted by eight methyl or methoxy groups.

5. A compound according to claim 1, which is $Z_2$[Ru(Pc)bis(triphenylphosphine monosulfonate)] wherein Z is a counterion.

6. A pharmaceutical composition comprising a compound of formula I according to claim 1, in admixture or association with a pharmaceutically acceptable carrier or diluent.

7. In the photodynamic therapy of cancer wherein a dye compound is administered to a tumor-bearing subject, the improvement which comprises using, as the dye compound, a compound according to claim 1.

* * * * *